(12) United States Patent
Ichihara et al.

(10) Patent No.: US 10,645,266 B2
(45) Date of Patent: May 5, 2020

(54) STEREO IMAGE PICKUP UNIT

(71) Applicant: OLYMPUS CORPORATION, Tokyo (JP)

(72) Inventors: Hirokazu Ichihara, Hino (JP); Hiroshi Unsai, Hachioji (JP); Toshiyuki Fujii, Machida (JP); Mayumi Imai, Hachioji (JP); Teruyuki Nishihara, Suginami-ku (JP); Jumpei Arai, Kitamoto (JP); Masahiro Sato, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/289,781

(22) Filed: Mar. 1, 2019

(65) Prior Publication Data

US 2019/0199895 A1 Jun. 27, 2019

Related U.S. Application Data

(63) Continuation of application No. PCT/JP2017/031179, filed on Aug. 30, 2017.

(30) Foreign Application Priority Data

Dec. 26, 2016 (JP) ................................. 2016-251715

(51) Int. Cl.
*H04N 5/225* (2006.01)
*A61B 1/05* (2006.01)
(Continued)

(52) U.S. Cl.
CPC ....... *H04N 5/2253* (2013.01); *A61B 1/00193* (2013.01); *A61B 1/051* (2013.01);
(Continued)

(58) Field of Classification Search
CPC ........ H04N 5/2253; H04N 7/18; H04N 5/225; H04N 13/204; H04N 5/2258;
(Continued)

(56) References Cited

U.S. PATENT DOCUMENTS 5,860,912 A * 1/1999 Chiba ................ A61B 1/00059
600/111
6,567,115 B1 * 5/2003 Miyashita .............. A61B 1/051
348/76
(Continued)

FOREIGN PATENT DOCUMENTS

JP H07-323004 A 12/1995
JP 2000-199863 A 7/2000
(Continued)

OTHER PUBLICATIONS

International Search Report dated Nov. 21, 2017 issued in PCT/JP2017/031179.

*Primary Examiner* — Yogesh K Aggarwal
(74) *Attorney, Agent, or Firm* — Scully, Scott, Murphy & Presser, P.C.

(57) ABSTRACT

A stereo image pickup unit includes: first and second image pickup apparatuses including first and second image pickup devices and first and second mount boards, the image pickup apparatuses being formed in a same shape each other; and a holding frame for holding the first and second image pickup devices, the first and second mount boards including non-mounting surfaces perpendicular to rear surfaces of the first and second image pickup devices and projecting toward an outer side of projection surfaces of the first and second image pickup devices, the holding frame holding the first and second image pickup apparatuses such that the non-mounting surfaces are opposed to each other on a parallax direction inner side.

4 Claims, 17 Drawing Sheets

(51) Int. Cl.
  *A61B 1/00* (2006.01)
  *G02B 23/26* (2006.01)
  *H04N 13/204* (2018.01)
  *H04N 7/18* (2006.01)
  *G02B 23/24* (2006.01)
  *G03B 35/00* (2006.01)

(52) U.S. Cl.
  CPC .............. *A61B 1/053* (2013.01); *G02B 23/24* (2013.01); *G02B 23/26* (2013.01); *G03B 35/00* (2013.01); *H04N 5/2252* (2013.01); *H04N 5/2257* (2013.01); *H04N 5/2258* (2013.01); *H04N 7/18* (2013.01); *H04N 13/204* (2018.05); *H04N 2005/2255* (2013.01)

(58) Field of Classification Search
  CPC ......... H04N 5/2252; H04N 2005/2255; H04N 13/239; G03B 35/00; G03B 17/55; G03B 35/08; G02B 23/24; G02B 23/26; G02B 7/021; G02B 23/2423; A61B 1/00193; A61B 1/051; A61B 1/053
  USPC ...................................................... 348/42–45
  See application file for complete search history.

(56) References Cited

U.S. PATENT DOCUMENTS

| | | | |
|---|---|---|---|
| 8,608,645 B2* | 12/2013 | Boebel | A61B 1/00193 600/111 |
| 2004/0167378 A1 | 8/2004 | Ando | |
| 2005/0267328 A1 | 12/2005 | Blumzvig et al. | |
| 2014/0350338 A1* | 11/2014 | Tanaka | A61B 1/00009 600/111 |
| 2016/0259159 A1* | 9/2016 | Matsui | G02B 23/26 |

FOREIGN PATENT DOCUMENTS

| | | |
|---|---|---|
| JP | 2000-258698 A | 9/2000 |
| JP | 2004-248957 A | 9/2004 |
| JP | 2005-525896 A | 9/2005 |
| WO | WO 03/098913 A2 | 11/2003 |

\* cited by examiner

STEREO IMAGE PICKUP UNIT

CROSS REFERENCE TO RELATED APPLICATION

This application is a continuation application of PCT/JP2017/031179 filed on Aug. 30, 2017 and claims benefit of Japanese Application No. 2016-251715 filed in Japan on Dec. 26, 2016, the entire contents of which are incorporated herein by this reference.

BACKGROUND OF INVENTION

1. Field of the Invention

The present invention relates to a stereo image pickup unit capable of acquiring two picked-up images having a parallax.

2. Description of the Related Art

In recent years, in fields of a medical endoscope and an industrial endoscope, there have been increasing needs for stereoscopically observing a subject using a stereo image pickup unit.

For example, as disclosed in Japanese Patent Application Laid-Open Publication No. 2000-199863, a stereo image pickup unit used at a distal end portion of an endoscope is configured by disposing, in a pair in a left-right direction, image pickup units including optical lens systems formed by pluralities of lens groups such as objective lenses, solid-state image pickup chips (image pickup devices), and circuit boards (mount boards) on which circuit components such as capacitors, transistors, and resistors are mounted.

Further, Japanese Patent Application Laid-Open Publication No. 2000-199863 discloses a technique for configuring a device board and electronic components and terminal sections of signal cables mounted on the device board to be fit in a projection area of a solid-state image pickup chip in order to achieve a reduction in a diameter of an endoscope.

SUMMARY OF THE INVENTION

A stereo image pickup unit according to an aspect of the present invention is a stereo image pickup unit including: a pair of objective optical systems disposed having a parallax; a pair of image pickup apparatuses each including an image pickup device and a substrate connected to rear surface of the image pickup device; and a holding member configured to hold the pair of image pickup apparatuses such that optical images respectively formed by the pair of objective optical systems are guided to the image pickup devices of the pair of image pickup apparatuses. The pair of image pickup apparatuses is formed in a same shape each other. The substrate included in each of the pair of image pickup apparatuses includes a plurality of surface sections perpendicular to the rear surface of the image pickup device. The plurality of surface sections include surface sections projecting from a direction of one side of the image pickup device toward an outer side of a projection surface of the image pickup device and formed by unmounting surfaces on which a component is not mounted. The holding member holds the pair of image pickup apparatuses such that the surface sections projecting toward the outer side of the projection surface are opposed to one another on a parallax direction inner side. The substrate is a laminated substrate in which a plurality of circuit boards are laminated in the parallax direction

DETAILED DESCRIPTION OF THE PREFERRED EMBODIMENT(S)

Figure 1:
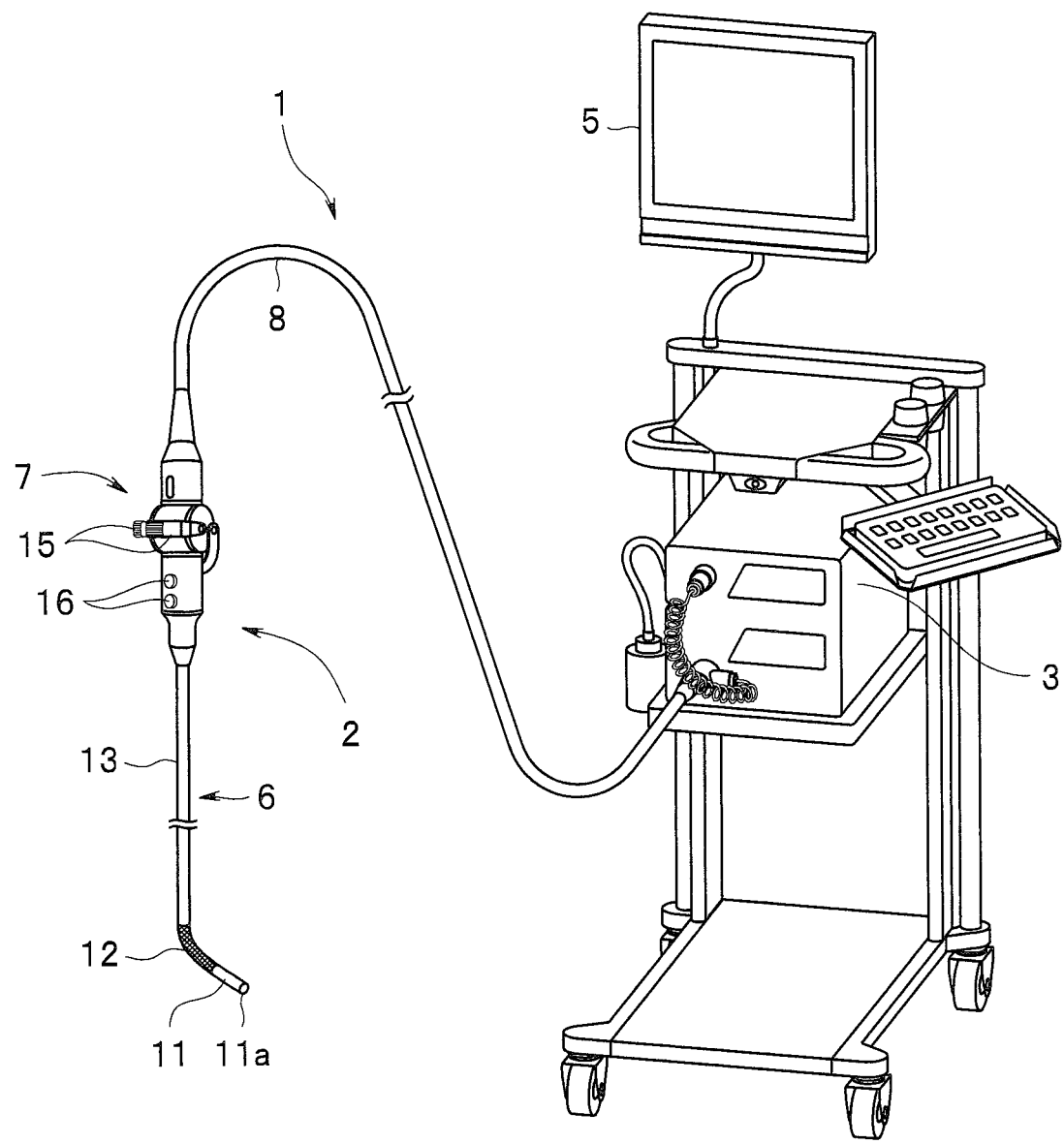
FIG. 1 relates to an embodiment of the present invention and is a perspective view showing an overall configuration of an endoscope system.
Figure 2:
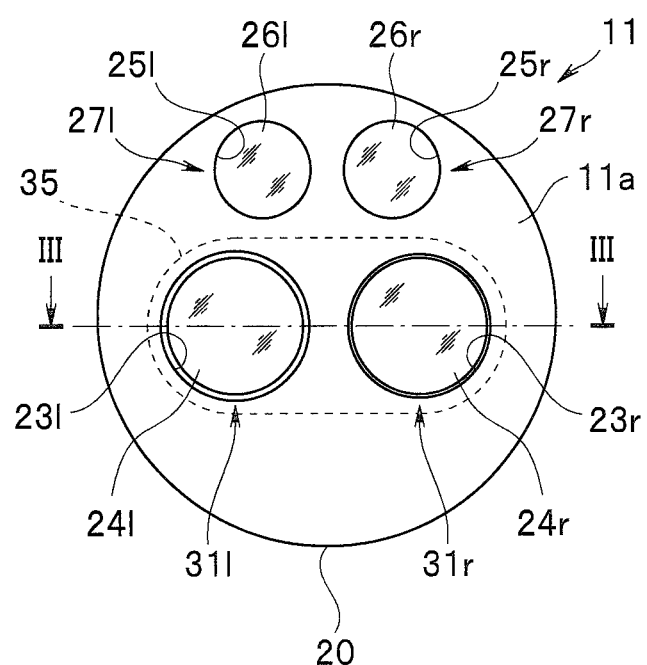
FIG. 2 relates to the embodiment of the present invention and is an end face view of a distal end portion of an endoscope.
Figure 3:
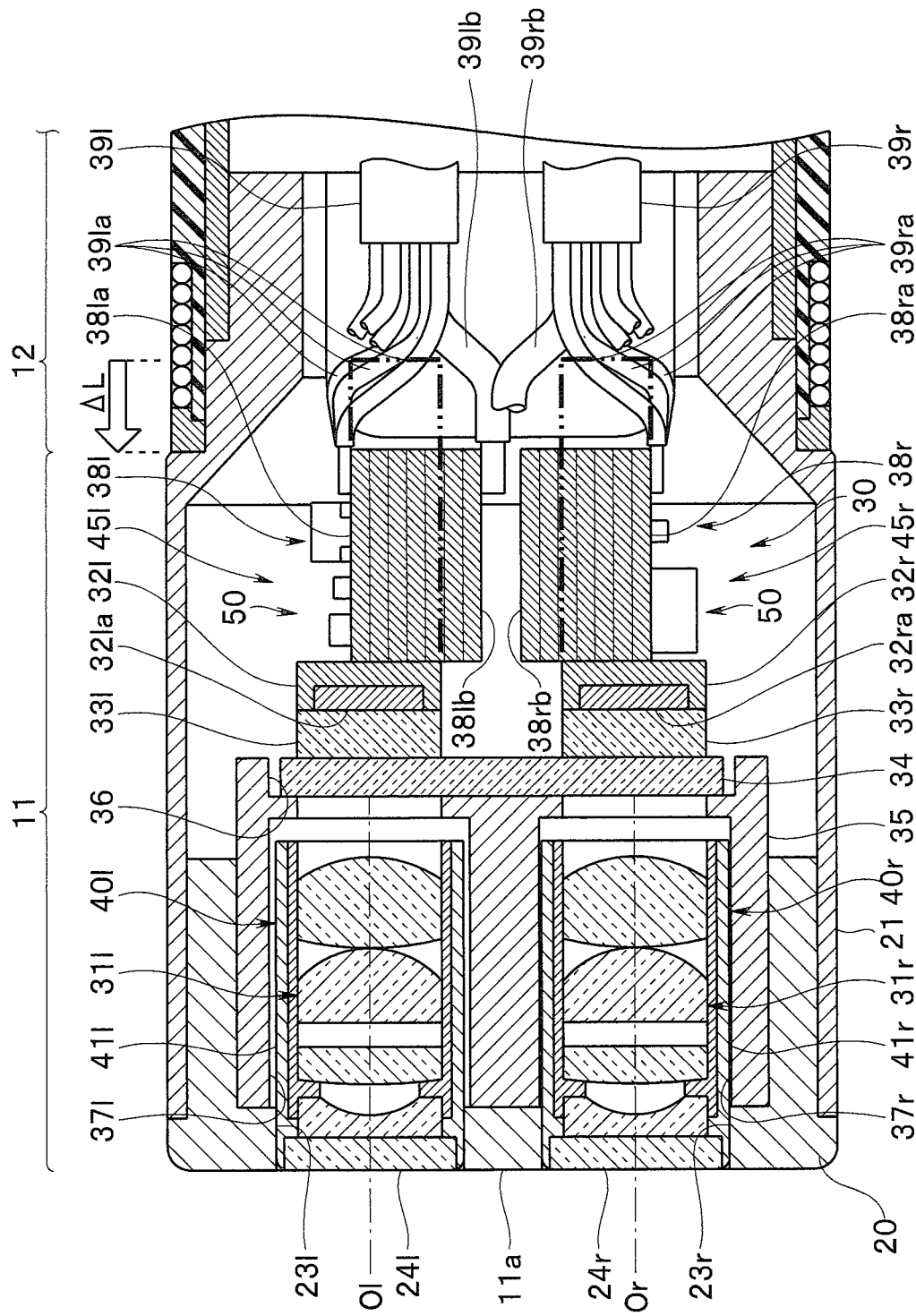
FIG. 3 relates to the embodiment of the present invention and is a III-III sectional view of FIG. 2.
Figure 4:
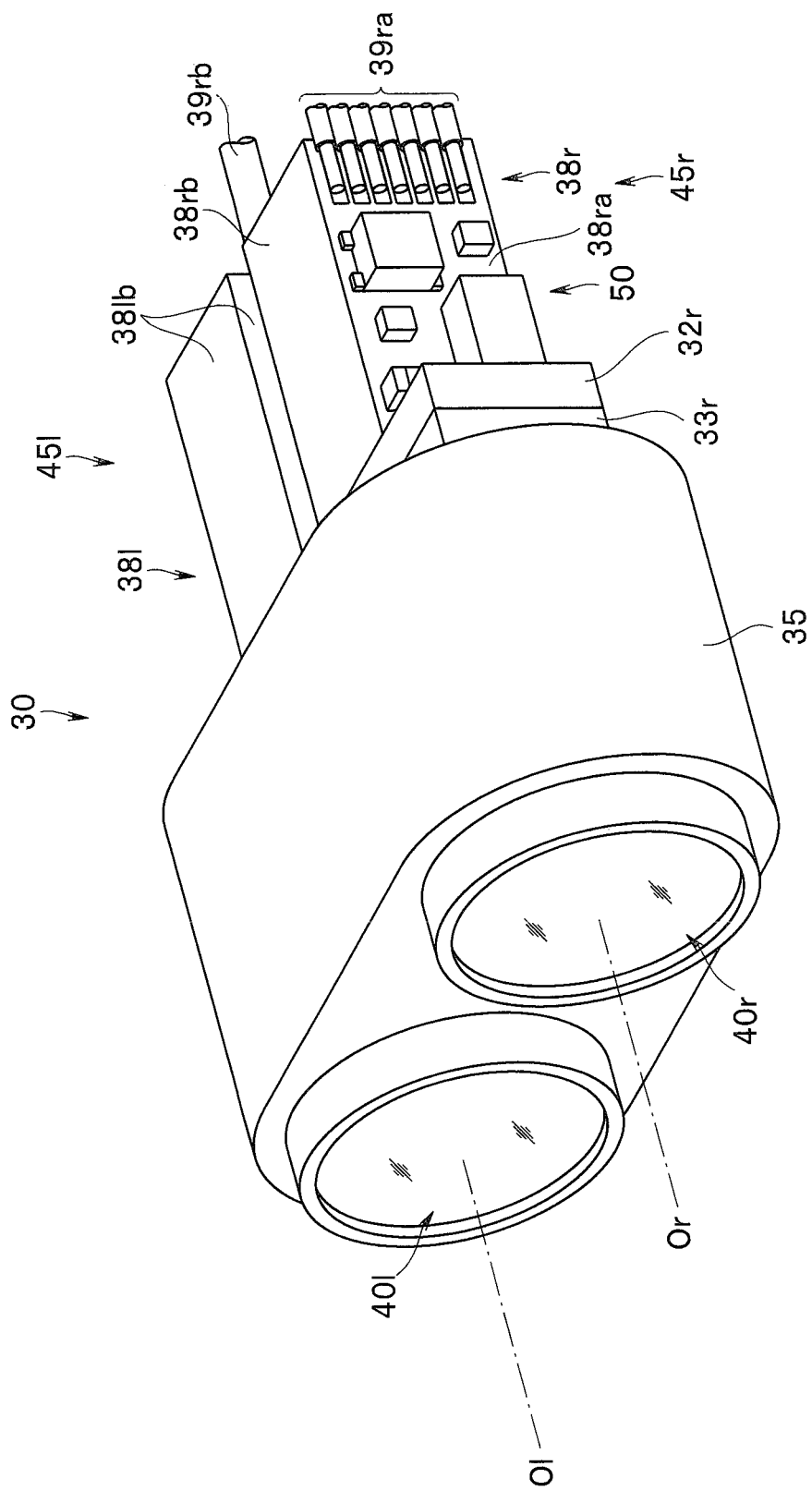
FIG. 4 relates to the embodiment of the present invention and is a perspective view of a stereo image pickup unit.
Figure 5:
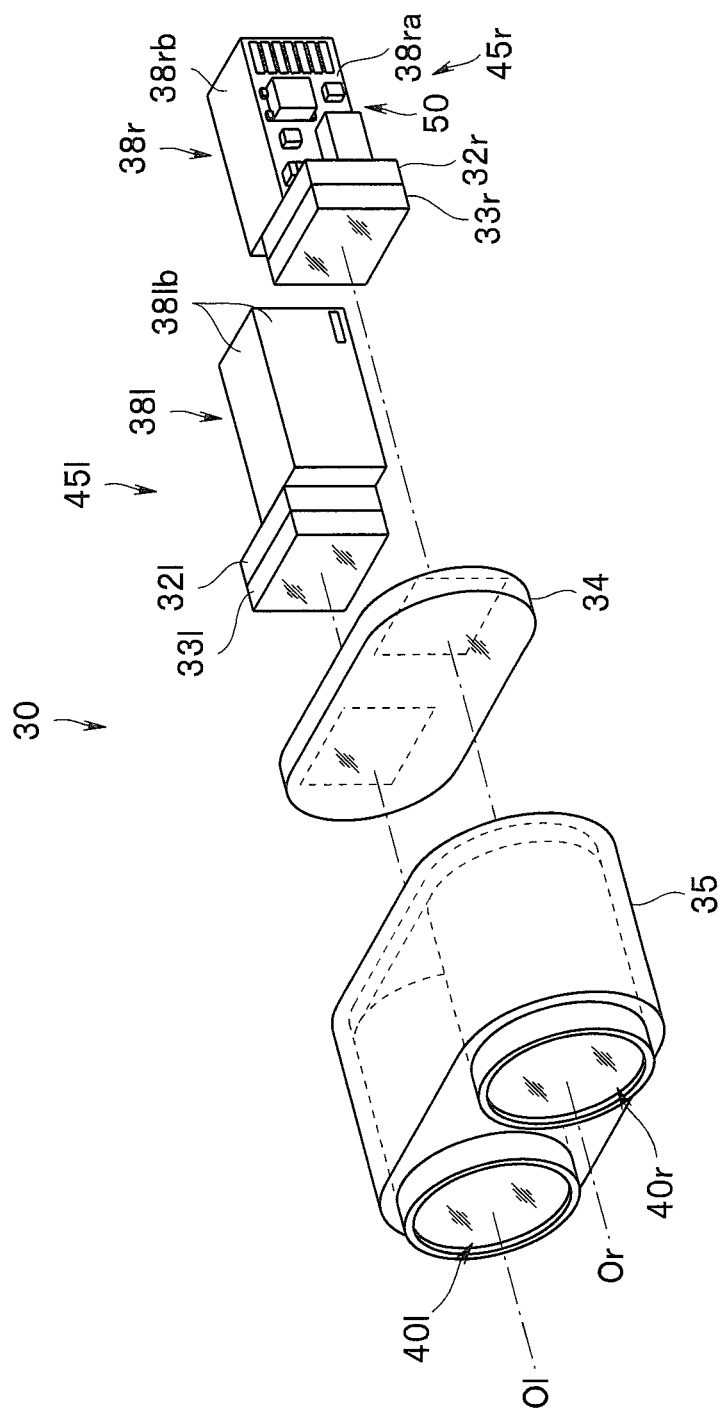
FIG. 5 relates to the embodiment of the present invention and is an exploded perspective view of the stereo image pickup unit.
Figure 6:
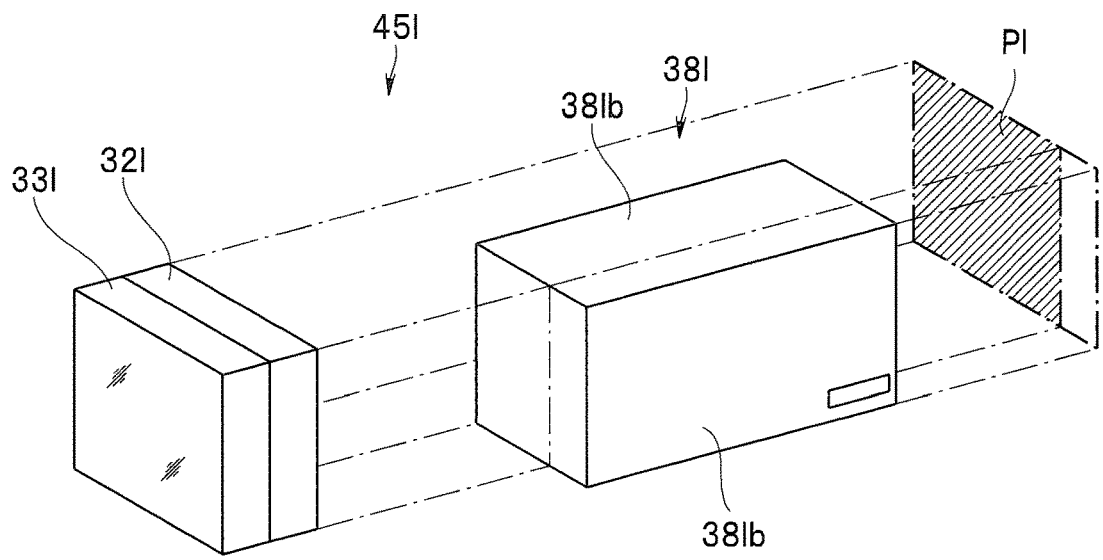
FIG. 6 relates to the embodiment of the present invention and is an exploded perspective view showing a positional relation between a projection surface of a first image pickup device and a first mount board.
Figure 7:
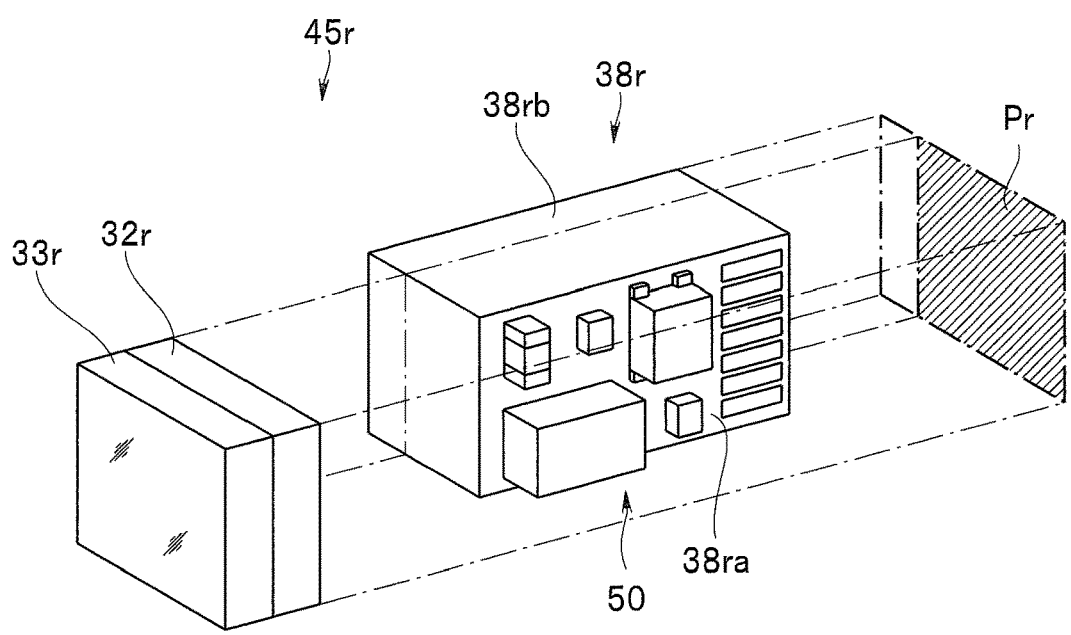
FIG. 7 relates to the embodiment of the present invention and is an exploded perspective view showing a positional relation between a projection surface of a second image pickup device and a second mount board.
Figure 8:
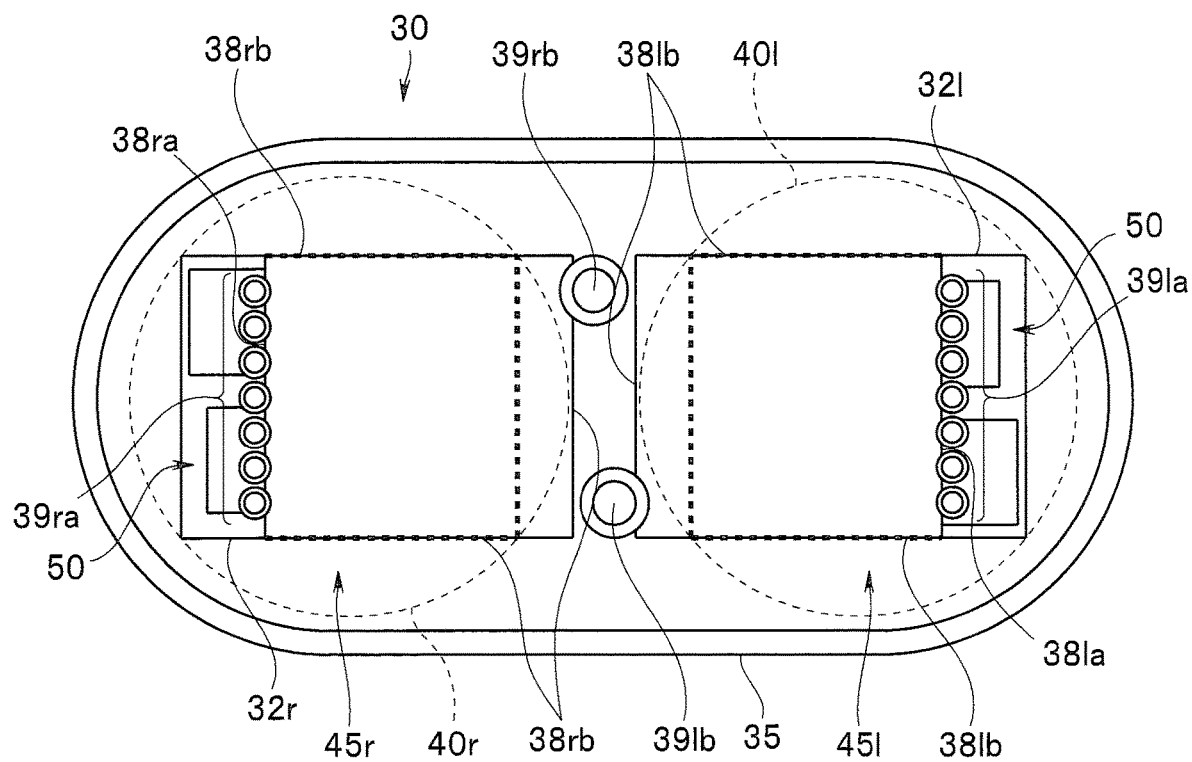
FIG. 8 relates to the embodiment of the present invention and is a rear view of the stereo image pickup unit.

A form of the present invention is explained below with reference to the drawings. FIG. 1 to FIG. 8 relate to an embodiment of the present invention. FIG. 1 is a perspective view showing an overall configuration of an endoscope system. FIG. 2 is an end face view of a distal end portion of an endoscope. FIG. 3 is a III-III sectional view of FIG. 2. FIG. 4 is a perspective view of a stereo image pickup unit. FIG. 5 is an exploded perspective view of the stereo image pickup unit. FIG. 6 is an exploded perspective view showing a positional relation between a projection surface of a first image pickup device and a first mount board. FIG. 7 is an exploded perspective view showing a positional relation between a projection surface of a second image pickup device and a second mount board. FIG. 8 is a rear view of the stereo image pickup unit.

An endoscope system 1 shown in FIG. 1 includes a stereoscopic endoscope 2 capable of stereoscopically picking up images of a subject from different visual points, a processor 3 to which the stereoscopic endoscope 2 is detachably connected, and a monitor 5 functioning as a display apparatus that displays, as an endoscopic image, an image signal generated by the processor 3.

The stereoscopic endoscope 2 in the present embodiment is, for example, a rigid endoscope applied to laparoscopic surgery. The stereoscopic endoscope 2 includes an elongated insertion section 6, an operation section 7 concatenated to a proximal end side of the insertion section 6, and a universal cable 8 extending from the operation section 7 and connected to the processor 3.

A distal end portion 11 mainly configured by a member made of metal such as stainless steel, a bending section 12, and a rigid tube section 13 configured by a tube of metal such as stainless steel are concatenated in the insertion section 6 in order from a distal end side.

The insertion section 6 is a portion inserted into a body. A stereo image pickup unit 30 (see FIG. 3) for stereoscopically picking up an image of an inside of a subject is incorporated in the distal end portion 11. Image pickup cable bundles 39*l* and 39*r* (see FIG. 3) electrically connected to the stereo image pickup unit 30, a light guide bundle (not shown in the figure) that transmits illumination light to the distal end portion 11, and the like are inserted through insides of the bending section 12 and the rigid tube section 13. Note that the stereoscopic endoscope 2 in the present embodiment illustrates a rigid endoscope, a proximal end side of which further than the bending section 12 is configured by the rigid tube section 13. However, the stereoscopic endoscope 2 is not limited to this and may be a flexible endoscope, a proximal end side of which further than the bending section 12 is configured by a flexible tube section having flexibility.

Note that, in the following explanation, an up-down direction and a left-right direction of respective sections refer to an up-down direction and a left-right direction corresponding to an up-down direction and a left-right direction of an image picked up by the stereo image pickup unit 30 and displayed on the monitor 5.

Angle levers 15 for remotely operating the bending section 12 are provided in the operation section 7. Further, various switches 16 for operating a light source device, a video system sensor, and the like of the processor 3 are provided.

The angle levers 15 are bending operation means capable of performing bending operation of the bending section 12 of the insertion section 6 in up, down, left, and right four directions here. Note that the bending section 12 is not limited to be configured to be bendable in the up, down, left, and right four directions and may be configured to be bendable in, for example, only up and down two directions or left and right two directions.

A configuration of a distal end portion of such a stereoscopic endoscope 2 is explained in detail with reference to FIGS. 2 and 3.

As shown in FIG. 3, the distal end portion 11 includes a distal end portion main body 20 formed in a substantially columnar shape and a distal end cylinder body 21 formed in a substantially cylindrical shape, a distal end of which is fixed to the distal end portion main body 20. The distal end of the distal end cylinder body 21 is fit in an outer periphery of the distal end portion main body 20. A distal end face 11*a* of the distal end portion 11 is formed by an end face of the distal end portion main body 20 exposed from the distal end cylinder body 21.

As shown in FIGS. 2 and 3, in the distal end portion main body 20, a pair of through-holes for observation 23*l* and 23*r* opening on the distal end face 11*a* is provided side by side on the left and the right (i.e., in a left and right bending direction by the bending section 12). A pair of objective optical systems (first and second objective optical systems 31*l* and 31*r*) configuring the stereo image pickup unit 30 is respectively held in the left and right respective through-holes for observation 23*l* and 23*r*. Consequently, observation windows 24*l* and 24*r* are formed on the distal end face 11*a* of the distal end portion 11.

For example, as shown in FIG. 2, above the through-holes for observation 23*l* and 23*r* (i.e., above in an up and down bending direction by the bending section 12), a pair of through-holes for illumination 25*l* and 25*r* opening on the distal end face 11*a* is provided side by side on the left and the right in the distal end portion main body 20. A pair of illumination optical systems 27*l* and 27*r* optically connected to a not-shown light guide bundle is respectively held in the left and right respective through-holes for illumination 25*l* and 25*r*. Consequently, illumination windows 26*l* and 26*r* are formed on the distal end face 11*a* of the distal end portion 11.

As shown in FIG. 3 to FIG. 5, the stereo image pickup unit 30 includes a first image pickup device 32*l* that receives an optical image (a first optical image) formed by the first objective optical system 31*l*, a second image pickup device 32*r* that receives an optical image (a second optical image) formed by the second objective optical system 31*r*, a single centering glass 34 functioning as a holding member disposed on optical paths of the first and second optical images, respective light receiving surfaces 32*la* and 32*ra* sides of the first and second image pickup devices 32*l* and 32*r* being positioned and fixed on the centering glass 34 by bonding, and a holding frame 35 functioning as a holding member that holds the first and second image pickup devices 32*l* and 32*r* via the centering glass 34.

The first and second image pickup devices 32*l* and 32*r* are configured by a solid-state image pickup device such as a CCD (charge coupled device) or a CMOS (complementary metal oxide semiconductor). Cover glasses 33*l* and 33*r* for protecting the light receiving surfaces 32*la* and 32*ra* are stuck to the first and second image pickup devices 32*l* and 32*r*.

First and second mount boards 38*l* and 38*r* functioning as substrates are connected to rear surfaces of the first and second image pickup devices 32*l* and 32*r*. The first and second mount boards 38*l* and 38*r* are respectively electrically connected to the first and second image pickup devices 32*l* and 32*r* via terminal sections (not shown in the figures) provided in the first and second image pickup devices 32*l* and 32*r*. First and second image pickup sections 45*l* and 45*r*, which are first and second image pickup apparatuses, are respectively configured by the first and second image pickup devices 32*l* and 32*r* and the first and second mount boards 38*l* and 38*r*.

Various electronic components such as digital ICs for generating driving signals for the first and second image pickup devices 32*l* and 32*r*, nonvolatile memories (EEPROMs) having stored therein control parameters, capacitors for IC driving power supply stabilization for stabilizing driving power supplies for the ICs, and resistors are respectively mounted on the respective first and second mount boards 38*l* and 38*r* by soldering or the like. As the control parameters, serial numbers (manufacturing numbers of a manufacturer) of the image pickup devices, correction data for correcting a white flaw of the image pickup devices, and the like are included. If it is difficult to mount a nonvolatile memory to correspond to each of the first and second image pickup devices 32*l* and 32*r*, the control parameters of the two image pickup devices may be collectively stored in one nonvolatile memory. In this case, the nonvolatile memory only has to be mounted on a substrate provided in the operation section 7 or in an inside of the endoscope other than the operation section 7. Image pickup cable bundles 39*l* and 39*r* are electrically connected to the respective mount boards 38*l* and 38*r*.

The centering glass 34 is configured by a transparent glass substrate extending in the left-right direction of the distal end portion 11. The light receiving surfaces 32*la* and 32*ra* sides of the first and second image pickup devices 32*l* and 32*r* are fixed to the centering glass 34 via the cover glasses 33*l* and 33*r*, respectively.

More specifically, the cover glasses 33*l* and 33*r* stuck to the light receiving surfaces 32*la* and 32*ra* are bonded to the centering glass 34 via an ultraviolet-curing transparent adhesive (a UV adhesive) or the like, whereby the first and second image pickup devices 32*l* and 32*r* are positioned and fixed in a state in which the first and second image pickup devices 32*l* and 32*r* are separated by a predetermined interval from each other.

The holding frame 35 is configured by a columnar metal member, a sectional shape of which is formed in a substantially rounded rectangular shape, (see, for example, FIG. 5). A glass holding section 36 is recessed on a proximal end side of the holding frame 35. The centering glass 34 is fixed to the glass holding section 36 by an adhesive or the like.

For example, as shown in FIGS. 3 and 5, a first objective optical system holding hole 37*l* and a second objective optical system holding hole 37*r* are provided side by side at a preset interval apart from each other in the holding frame 35. The first and second objective optical system holding holes 37*l* and 37*r* are configured by through-holes, distal end sides of which are opened on an end face (the distal end face 11*a*) of the holding frame 35 and proximal end sides of which communicate with the glass holding section 36.

The first and second objective optical systems 31*l* and 31*r* are respectively held in the first and second objective optical system holding holes 37*l* and 37*r* while having a predetermined parallax in a state in which the first and second objective optical systems 31*l* and 31*r* are unitized as first and second objective optical system units 40*l* and 40*r*.

That is, the first and second objective optical systems 31*l* and 31*r* are respectively held by first and second lens frames 41*l* and 41*r* to thereby configure the first and second objective optical system units 40*l* and 40*r*. The first and second objective optical system units 40*l* and 40*r* are positioned and fixed via an adhesive or the like in the first and second objective optical system holding holes 37*l* and 37*r*, whereby the first and second objective optical systems 31*l* and 31*r* are integrally held by the single holding frame 35 together with the first and second image pickup devices 32*l* and 32*r*.

A specific configuration of the first and second image pickup sections 45*l* and 45*r* is explained with reference to FIG. 3 to FIG. 8.

In the present embodiment, the first and second image pickup sections 45*l* and 45*r* are respectively module components formed in the same shape each other respectively configured by image pickup devices and mount boards formed in common specifications and a common shape. The first and second image pickup sections 45*l* and 45*r* are held by the holding frame 35 (the centering glass 34) in a state in which the first and second image pickup sections 45*l* and 45*r* are reversed 180 degrees with respect to each other (i.e., for example, in a state in which [with respect to the first image pickup section 45*l*, which is one image pickup section] the second image pickup section 45*r*, which is the other image pickup section, is rotated 180 degrees around an optical axis O*r*). Note that, when the first and second image pickup devices 32*l* and 32*r* configuring the first and second image pickup sections 45*l* and 45*r* are CMOSs, order for reading out image pickup signals from the first and second image pickup devices 32*l* and 32*r* is set such that the image pickup signals are reversed.

As shown in FIG. 3, the first and second mount boards 38*l* and 38*r* in the present embodiment are configured by laminated substrates in which pluralities of circuit boards are laminated in a parallax direction. That is, the first and second mount boards 38*l* and 38*r* are configured by hard bulk-like laminated substrates formed in a substantially cubic shape having planar surface sections respectively in the up-down direction and the left-right direction of optical axes O*l* and O*r*.

Surface sections on a parallax direction outer side among respective surface sections of the first and second mount boards 38*l* and 38*r* are set as mounting surfaces 38*la* and 38*ra*. Pluralities of lands are formed on the respective mounting surfaces 38*la* and 38*ra* of the first and second mount boards 38*l* and 38*r*. Various electronic components 50 are mounted on the respective mounting surfaces 38*la* and 38*ra* of the first and second mount boards 38*l* and 38*r* via the respective lands. Various signal wires 39*la* and 39*ra* (excluding ground wires 39*lb* and 39*rb* explained below) branched from the image pickup cable bundles 39*l* and 39*r* are electrically connected to the respective mounting surfaces 38*la* and 38*ra*.

On the other hand, respective surface sections in the up-down direction and surface sections on a parallax direction inner side among the respective surface sections of the first and second mount boards 38*l* and 38*r* are set as the non-mounting surfaces 38*la* and 38*ra* on which various electronic components are not mounted. However, only lands for grounding are formed on the surface sections on the parallax direction inner side of the first and second mount boards 38*l* and 38*r*. The ground wires 39*lb* and 39*rb* branched from the image pickup cable bundles 39*l* and 39*r* are electrically connected to the surface sections via the lands for grounding.

As shown in FIG. 3 to FIG. 8, the first and second mount boards 38*l* and 38*r* configured in this way are concatenated to proximal end sides of the first and second image pickup devices 32*l* and 32*r* in a state in which the respective surface sections (non-mounting surfaces 38*lb* and 38*rb*) in the up-down direction and the various electronic components 50 mounted on the surface sections (the mounting surfaces 38*la* and 38*ra*) on the parallax direction outer side are positioned not to project to the up-down direction and the parallax direction outer side of projection surfaces Pl and Pr in the optical axes Ol and Or direction of the first and second image pickup devices 32*l* and 32*r* and the surface sections (the non-mounting surfaces 38*lb* and 38*rb*) on the parallax direction inner side are positioned to project to the outer side (the parallax direction inner side) from the projection surfaces Pl and Pr and to be opposed to each other.

That is, height in the up-down direction of the first and second mount boards 38*l* and 38*r* are set to substantially the same height as height of the first and second image pickup devices 32*l* and 32*r*. The first and second mount boards 38*l* and 38*r* are positioned such that the respective surface sections in the up-down direction extend substantially flush with upper surfaces and lower surfaces of the first and second image pickup devices 32*l* and 32*r*.

The first and second mount boards 38*l* and 38*r* are positioned such that the surfaces (the mounting surfaces 38*la* and 38*ra*) on the parallax direction outer side are offset further to the inner side than surfaces on the parallax direction outer side of the first and second image pickup devices 32*l* and 32*r*.

Further, the first and second mount boards 38*l* and 38*r* are positioned such the surface sections (the non-mounting surfaces 38*lb* and 38*rb*) on the parallax direction inner side are offset further to the outer sides than surfaces on the parallax direction inner side of the first and second image pickup devices 32*l* and 32*r* within a range in which the surface sections (the non-mounting surfaces 38*lb* and 38*rb*) on the parallax direction inner side are not in contact with each other.

In other words, the first and second mount boards 38*l* and 38*r* are configured by laminated substrates in which pluralities of circuit boards are laminated in the parallax direction without causing various electronic components mounted on the surface sections on the parallax direction outer side to project from the projection surfaces Pl and Pr and within a range in which the surface sections on the parallax direction inner side are not in contact with each other. The pluralities of circuit boards are laminated to a position where the pluralities of circuit boards project to the parallax direction inner side. A volume (an effective circuit area) of the laminated substrates is secured. Consequently, length in the optical axes Ol and Or direction of the first and second mount boards 38*l* and 38*r* is reduced by ΔL compared with when all of the surface sections and the various electronic components are fit within the projection surfaces Pl and Pr (see, alternate long and two short dashes lines in FIG. 3). As a result of reducing the length in the optical axes Ol and Or direction of the first and second mount boards 38*l* and 38*r* in this way, a hard length of the distal end portion 11 is also reduced.

According to such an embodiment, the first and second mount boards 38*l* and 38*r* including pluralities of surface sections perpendicular to the rear surfaces of the first and second image pickup devices 32*l* and 32*r* are connected to the rear surfaces of the first and second image pickup devices 32*l* and 32*r* to configure the first and second image pickup sections 45*l* and 45*r* formed in the same shape each other. Among the respective surface sections of the first and second mount boards 38*l* and 38*r*, one of the surface sections formed by each of the non-mounting surfaces 38*lb* and 38*rb* on which electronic components are not mounted is caused to project from a direction of one side of each of the first and second image pickup devices 32*l* and 32*r* toward the outer side of the projection surfaces Pl and Pr. The holding frame 35 (the centering glass 34) is caused to hold the first and second image pickup sections 45*l* and 45*r* in a state in which the first and second image pickup sections 45*l* and 45*r* are reversed 180 degrees around the optical axes Ol and Or from each other such that the projecting surface sections (the non-mounting surfaces) are opposed to each other in the parallax direction inner side. Consequently, it is possible to effectively reduce the hard length of the distal end portion 11 without increasing the distal end portion 11 in a diameter.

That is, the first and second mount boards 38*l* and 38*r* are positioned such that the respective surface sections (the non-mounting surfaces 38*lb* and 38*rb*) in the up-down direction and the various electronic components 50 mounted on the surface sections (the mounting surfaces 38*la* and 38*ra*) on the parallax direction outer side do not project to the up-down direction and the parallax direction outer side of the projection surfaces Pl and Pr of the first and second image pickup devices 32*l* and 32*r*. Further, the first and second mount boards 38*l* and 38*r* are concatenated to the proximal end sides of the first and second image pickup devices 32*l* and 32*r* in a state in which the surface sections on the parallax direction inner side are set as the non-mounting surfaces 38*lb* and 38*rb*, on which electronic components are not mounted, and positioned to project to the parallax direction inner side from the projection surfaces Pl and Pr and to be opposed to each other. Consequently, it is possible to effectively reduce the hard length of the distal end portion 11 without increasing the distal end portion 11 in a diameter.

In other words, the respective surface sections in the up-down direction of the first and second mount boards 38*l* and 38*r* and the various electronic components 50 mounted on the surface sections (the mounting surfaces 38*la* and 38*ra*) on the parallax direction outer side are positioned not to project to the up-down direction and the parallax direction outer side of the projection surfaces Pl and Pr of the first and second image pickup devices 32*l* and 32*r*. Consequently, it is possible to effectively prevent an increase in a diameter of the distal end portion 11. On the other hand, the surfaces (the non-mounting surfaces 38*lb* and 38*rb*) on the parallax direction inner side of the first and second mount boards 38*l* and 38*r* are positioned to project to the parallax direction inner side from the projection surfaces Pl and Pr to be opposed to each other. Consequently, it is possible to effectively utilize an interval set between the optical axes Ol and Or in order to secure a left-right parallax, without forming the interval as a dead space and secure a volume (an effective circuit area) of the first and second mount boards 38*l* and 38*r*. As a result, for example, it is possible to reduce length in the optical axes Ol and Or direction of the first and second mount boards 38*l* and 38*r* compared with when all of the surface sections and the various electronic components 50 are fit within the projection surfaces Pl and Pr (see, the alternate long and two short dashes lines in FIG. 3). Accordingly, it is possible to effectively reduce the hard length of the distal end portion 11.

In this case, the surface sections on the parallax direction inner side of the first and second mount boards 38*l* and 38*r* are set as the non-mounting surfaces 38*lb* and 38*rb* on which electronic components are not mounted. Consequently, even when the first and second mount boards 38*l* and 38*r* are brought close to the parallax direction inner side, it is possible to effectively prevent interference due to a so-called crosstalk or the like between electronic components on the first and the second mount boards 38*l* and 38*r*.

Further, the ground wires 39*lb* and 39*rb* are connected to the non-mounting surfaces 38*lb* and 38*rb* on the parallax direction inner side where the first and second mount boards 38*l* and 38*r* are opposed to each other. Consequently, even when the first and second mount boards 38*l* and 38*r* are brought close, it is possible to quickly radiate heat through the ground wires 39*lb* and 39*rb*. Further, it is possible to realize a shield effect against the crosstalk or the like and more effectively prevent the interference between the electronic components on the first and second mount boards 38*l* and 38*r*.

Further, the first and second image pickup sections 45*l* and 45*r* are formed in the same shape respectively configured by the image pickup devices and the mount boards respectively formed in the common specifications and the common shape. The first and second image pickup sections 45*l* and 45*r* are held by the centering glass 34 in a state in which with respect to one image pickup section the other image pickup section is rotated 180 degrees around the optical axis. Therefore, it is unnecessary to form the first and second image pickup sections 45*l* and 45*r* as dedicated components respectively for the left and the right. It is possible to effectively reduce a manufacturing manhour, manufacturing cost, and the like.

Figure 9:
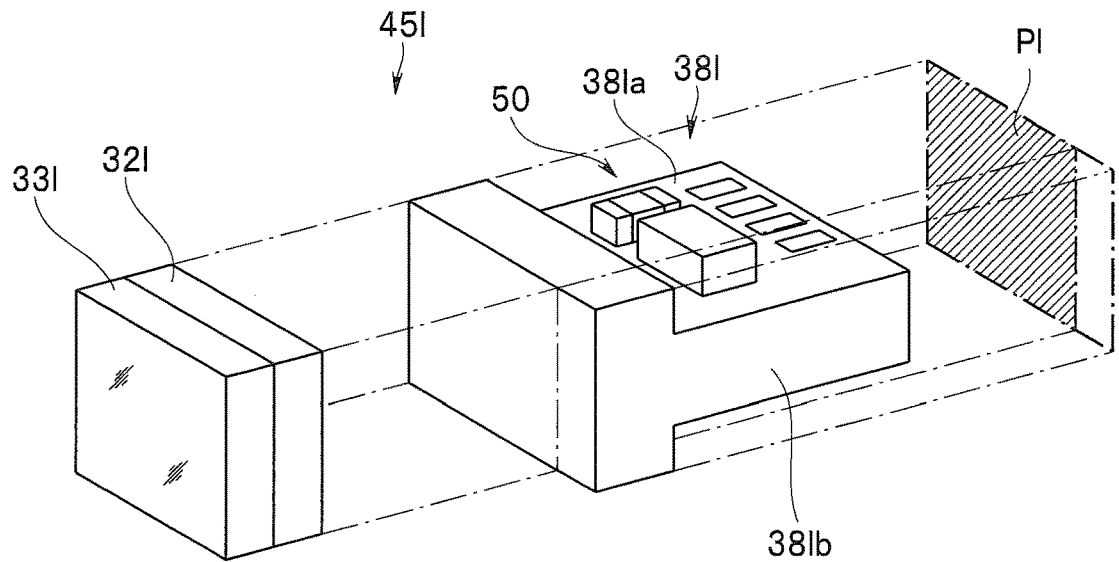
FIG. 9 relates to a first modification and is an exploded perspective view showing a positional relation between a projection surface of a first image pickup device and a first mount board.
Figure 10:
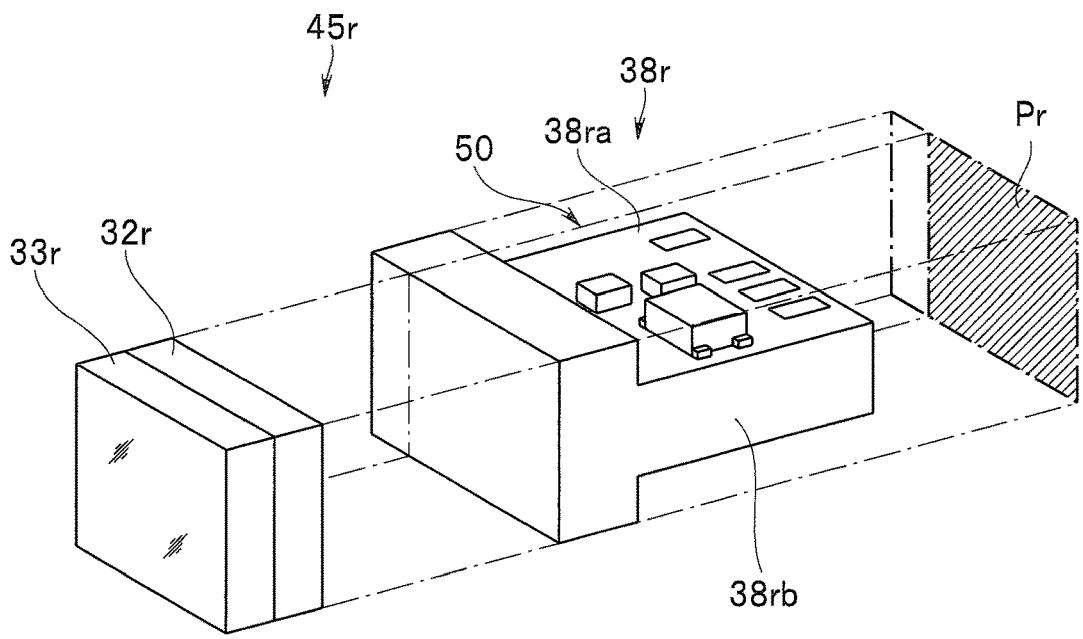
FIG. 10 relates to the first modification and is an exploded perspective view showing a positional relation between a projection surface of a second image pickup device and a second mount board.
Figure 11:
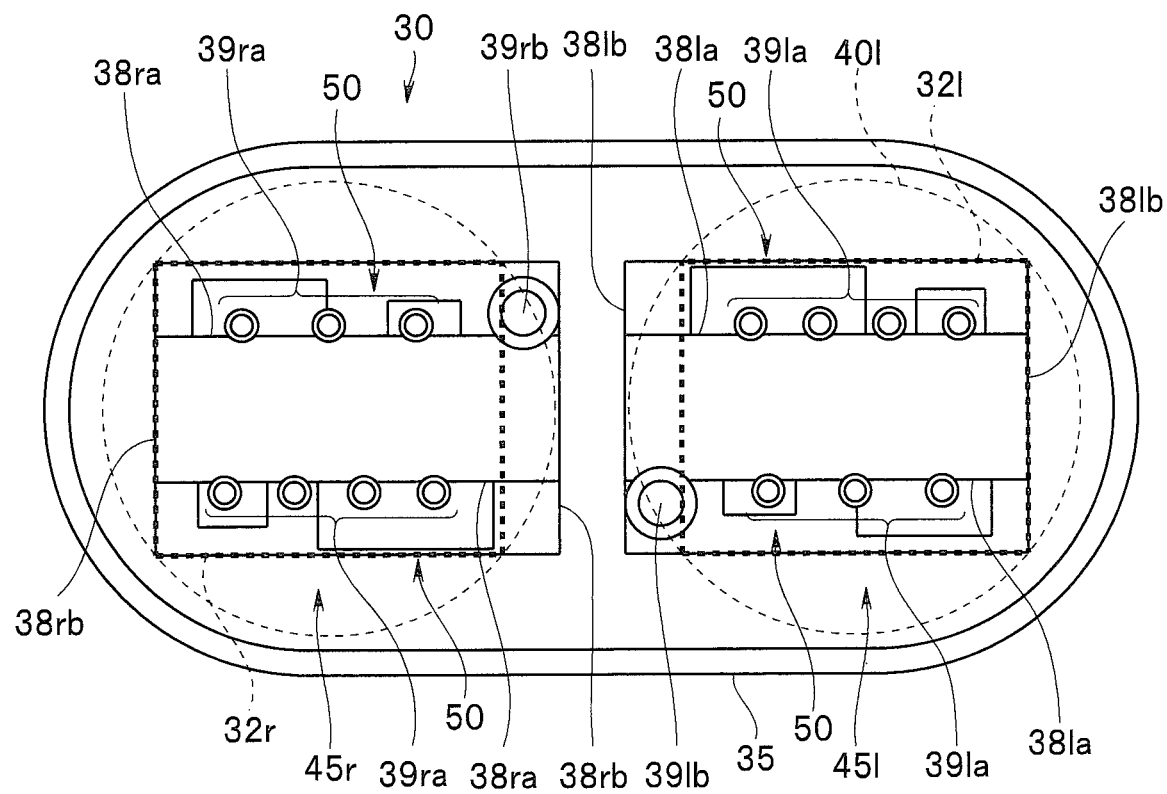
FIG. 11 relates to the first modification and is a rear view of a stereo image pickup unit.

For example, as shown in FIG. 9 to FIG. 11, the respective surface sections in the up-down direction of the first and second mount boards 38*l* and 38*r* are configured by stepped surface sections. Consequently, it is also possible to form the first and second mount boards 38*l* and 38*r* as irregular-shaped boards formed in a T shape in a side view.

With such a configuration, it is possible to effectively use the respective surface sections in the up-down direction of the first and second mount boards 38*l* and 38*r* as the mounting surfaces 38*la* and 38*ra*.

Figure 12:
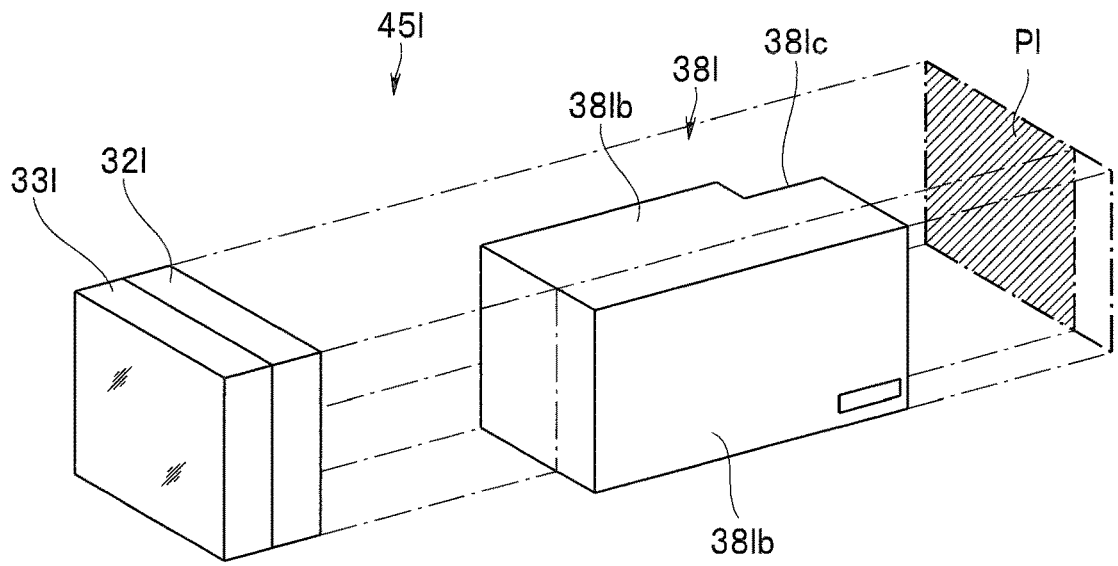
FIG. 12 relates to a second modification and is an exploded perspective view showing a positional relation between a projection surface of a first image pickup device and a first mount board.
Figure 13:
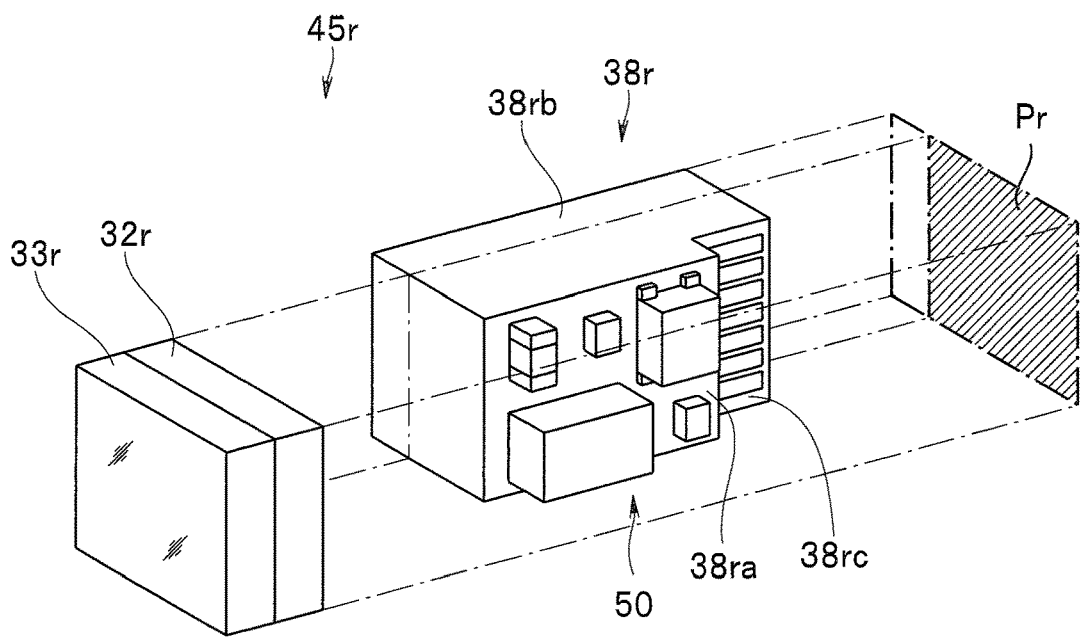
FIG. 13 relates to the second modification and is an exploded perspective view showing a positional relation between a projection surface of a second image pickup device and a second mount board.
Figure 14:
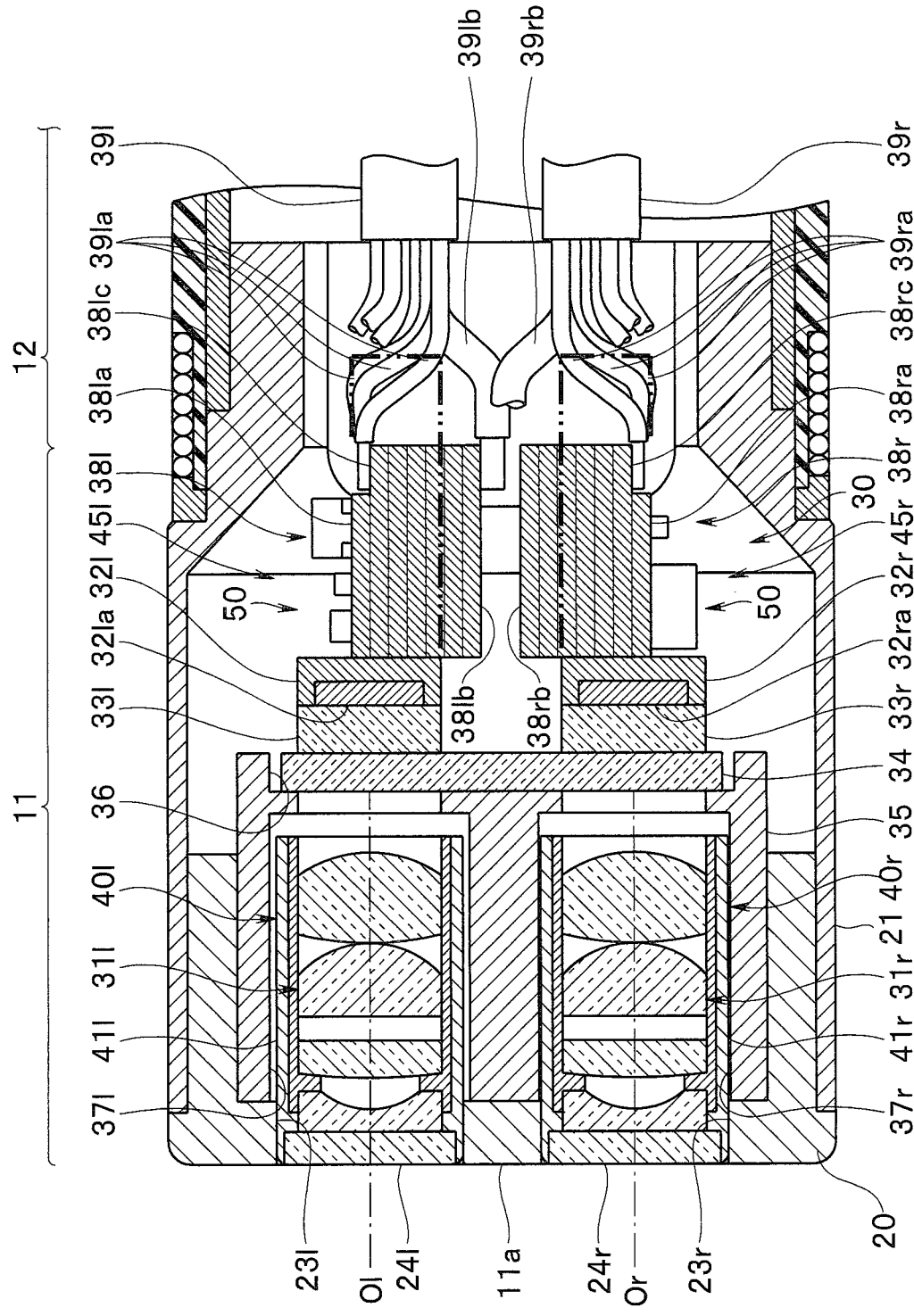
FIG. 14 relates to the second modification and is a main part sectional view of a distal end portion.
Figure 15:
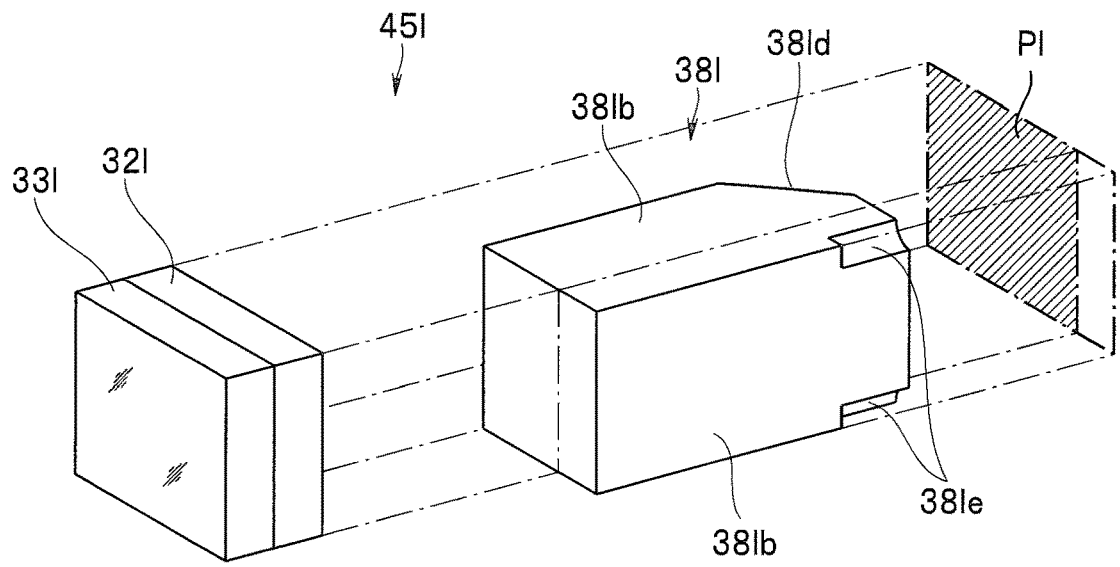
FIG. 15 relates to a third modification and is an exploded perspective view showing a positional relation between a projection surface of a first image pickup device and a first mount board.
Figure 16:
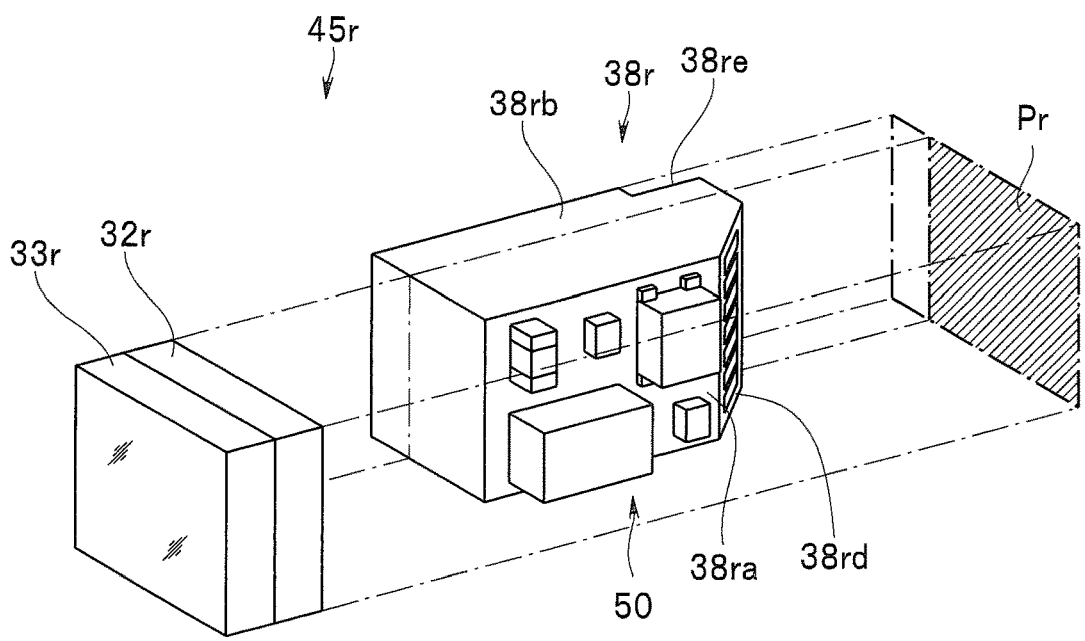
FIG. 16 relates to the third modification and is an exploded perspective view showing a positional relation between a projection surface of a second image pickup device and a second mount board.

For example, as shown in FIG. 12 to FIG. 14, it is also possible to form step sections 38*lc* and 38*rc* on proximal end sides of the respective surface sections (the mounting surfaces) on the parallax direction outer side of the first and second mount boards 38*l* and 38*r* and provide, in the respective step sections 38*lc* and 38*rc*, lands for electrically connecting the various signal wires 39*la* and 39*ra*.

With such a configuration, it is possible to more effectively avoid the interference between the distal end cylinder body 21 and the various signal wires 39*la* and 39*ra* on a proximal end side of the distal end portion 11. It is possible to more effectively reduce the hard length of the distal end portion 11.

From the same reason, for example, as shown in FIG. 15 to FIG. 18, it is also possible to form inclined surfaces 38*ld* and 38*rd* on the proximal end sides of the respective surface sections (the mounting surfaces) on the parallax direction outer side of the first and second mount boards 38*l* and 38*r* and provide, on the respective inclined surfaces 38*ld* and 38*rd*, lands for electrically connecting the various signal wires 39*la* and 39*ra*.

In addition, it is also possible to provide a pair of upper and lower cutout sections 38*le* and 38*re* on the respective surface sections (the non-mounting surfaces) on the parallax direction inner side of the first and second mount boards 38*l* and 38*r* and provide lands for grounding in the respective cutout sections 38*le* and 38*re*.

Figure 17:
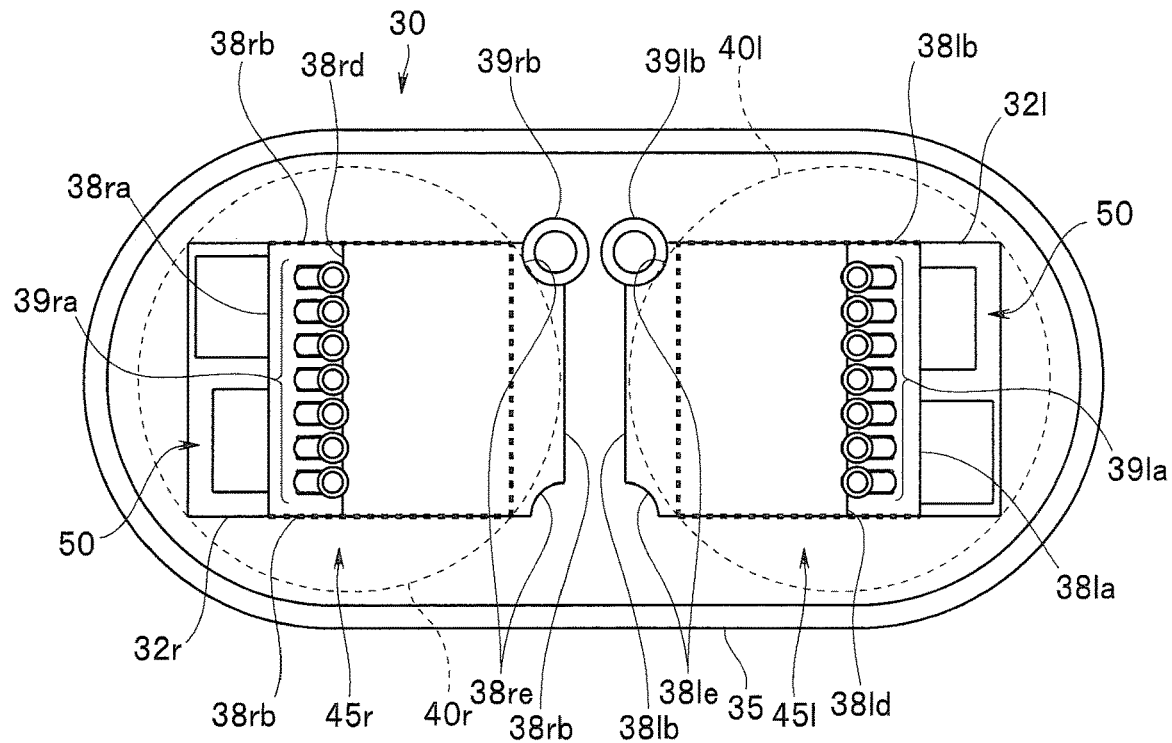
FIG. 17 relates to the third modification and is a rear view of a stereo image pickup unit.
Figure 18:
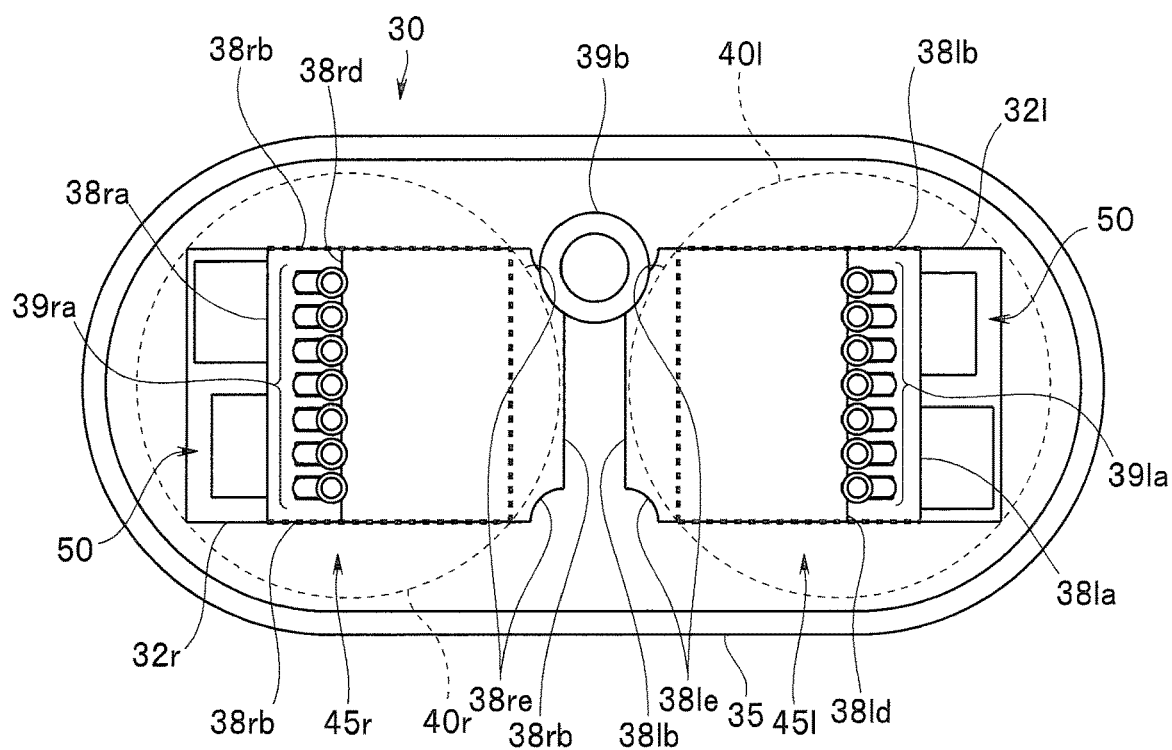
FIG. 18 relates to the third modification and is a rear view of the stereo image pickup unit.

With such a configuration, for example, as shown in FIG. 17, it is possible to connect the ground wires 39*lb* and 39*rb* to the first and second mount boards 38*l* and 38*r* from the same direction. Further, for example, as shown in FIG. 18, it is possible to connect a common ground wire 39*b* formed in a large diameter to the first and second mount boards 38*l* and 38*r*.

Figure 19:
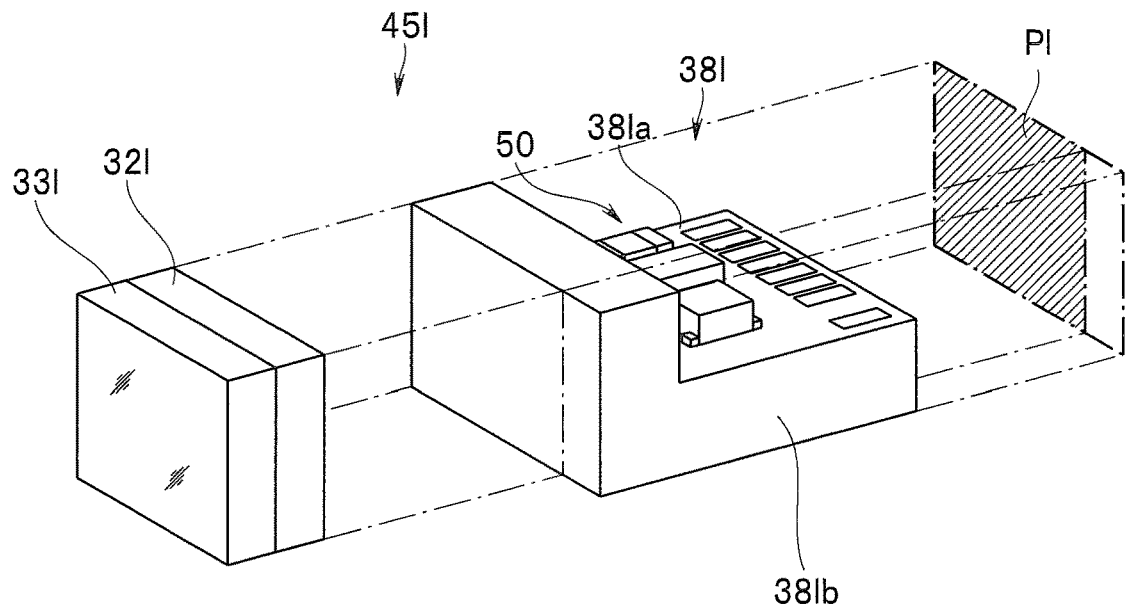
FIG. 19 relates to a fourth modification and is an exploded perspective view showing a positional relation between a projection surface of a first image pickup device and a first mount board.
Figure 20:
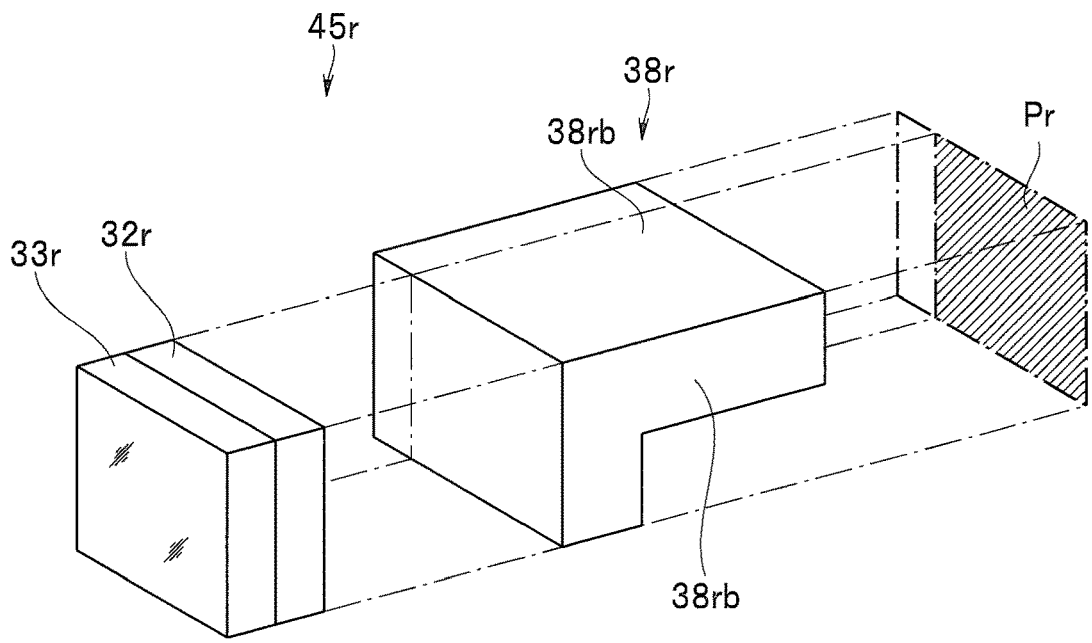
FIG. 20 relates to the fourth modification and is an exploded perspective view showing a positional relation between a projection surface of a second image pickup device and a second mount board.
Figure 21:
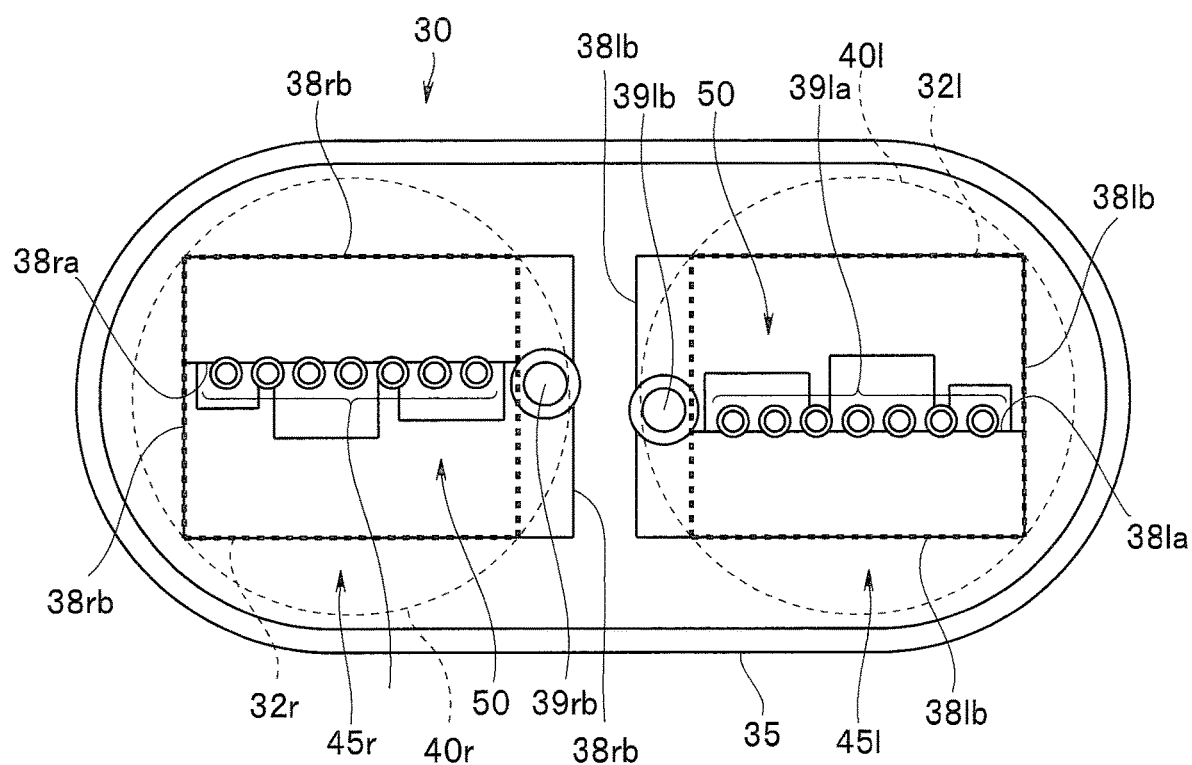
FIG. 21 relates to the fourth modification and is a rear view of a stereo image pickup unit.

For example, as shown in FIG. 19 to FIG. 21, a surface section in an upward direction of the first mount board 38*l* and a surface section in a downward direction of the second mount board 38*r* are configured by stepped surface sections. Consequently, it is also possible to form the first and second mount boards 38*l* and 38*r* as irregular-shaped boards formed in an L shape in a side view.

With such a configuration, it is possible to effectively use the respective surface sections in the up-down direction of the first and second mount boards 38*l* and 38*r* as the mounting surfaces 38*la* and 38*ra*. In addition, the surface section in the upward direction of the first mount board 38*l* and the surface section in the downward direction of the second mount board 38*r* are formed as the mounting surfaces 38*la* and 38*ra*. Consequently, even when either one of the mounting surfaces 38*la* and 38*ra* is directed to an upper side, for example, during assembly of the stereo image pickup unit 30, it is possible to cause a soldering iron to access the mounting surfaces 38*la* and 38*ra* from a right side. Therefore, it is possible to easily perform soldering work or the like by the soldering iron generally gripped by a right hand.

Figure 22:
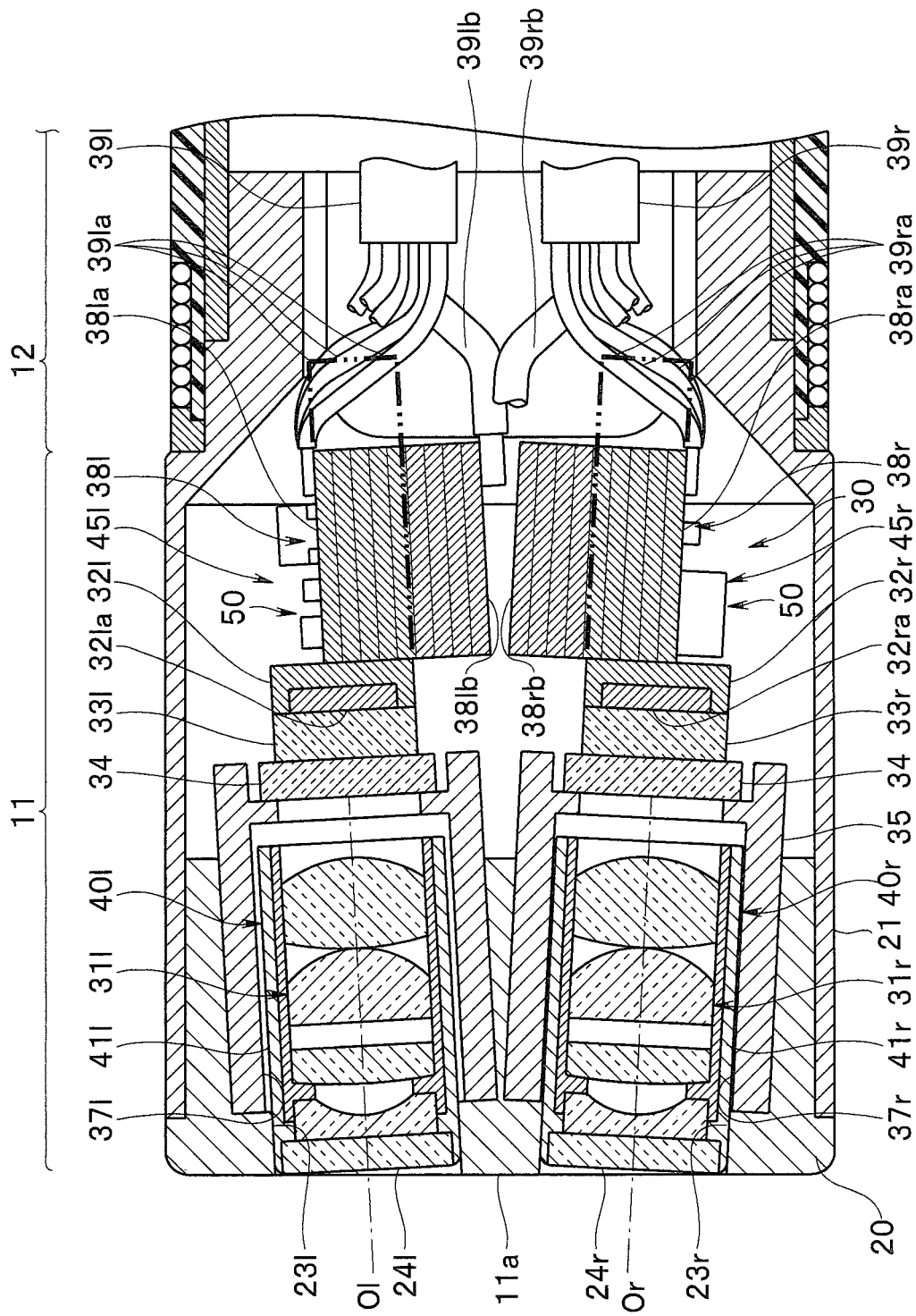
FIG. 22 relates to a fifth modification and is a main part sectional view of a distal end portion.

For example, as shown in FIG. 22, it is possible to adopt the same configuration as the configuration in the embodiment explained above in the stereo image pickup unit 30 of a so-called Greenough type in which the optical axes Ol and Or of the first and second objective optical system units 40*l* and 40*r* are set in non-parallel.

Figure 23:
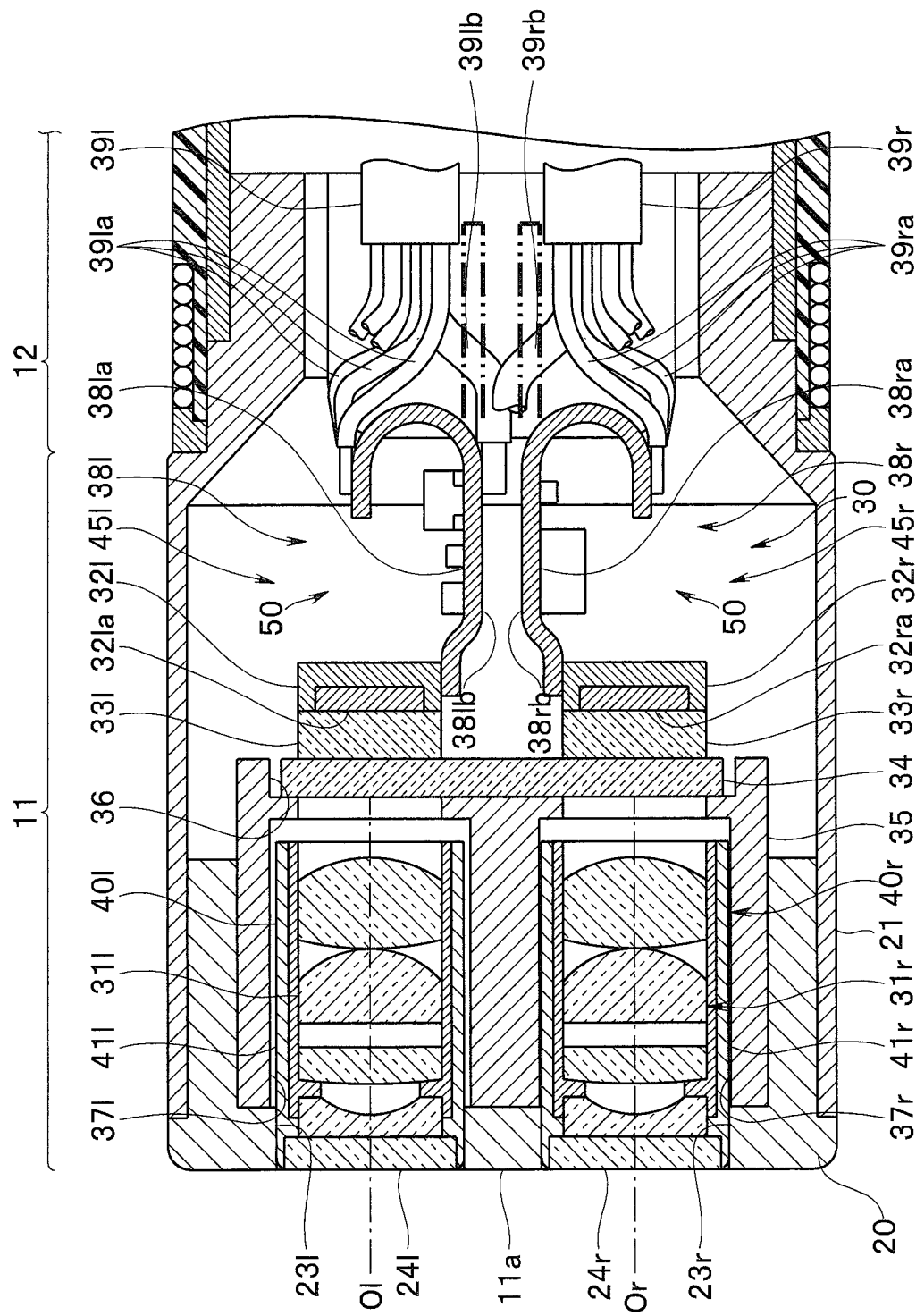
FIG. 23 relates to a sixth modification and is a main part sectional view of a distal end portion.

For example, as shown in FIG. 23, the first and second mount boards 38*l* and 38*r* are not limited to the hard laminated substrates and may be soft flexible substrates. In this case, the first and second mount boards 38*l* and 38*r* are disposed such that the non-mounting surfaces project to the parallax direction inner side with respect to the projection surfaces Pl and Pr. The proximal end sides of the first and second mount boards 38*l* and 38*r* are folded back to the parallax direction outer side. Consequently, it is possible to achieve substantially the same effects as the effects in the embodiment explained above.

Note that the present invention is not limited to the embodiments explained above. Various modifications and changes are possible. The modifications and changes are also within the technical scope of the present invention. For example, it goes without saying that the configurations of the embodiment and the respective modifications may be combined as appropriate.

What is claimed is:
1. A stereo image pickup unit comprising:
a pair of objective optical systems disposed having a parallax;
a pair of image pickup apparatuses each including an image pickup device and a substrate connected to rear surface of the image pickup device; and a holding member configured to hold the pair of image pickup apparatuses such that optical images respectively formed by the pair of objective optical systems are guided to the image pickup devices of the pair of image pickup apparatuses, wherein the pair of image pickup apparatuses is formed in a same shape with respect to each other, the substrate included in each of the pair of image pickup apparatuses includes a plurality of surface sections perpendicular to the rear surface of the image pickup device, the plurality of surface sections include surface sections projecting from a direction of one side of the image pickup device toward an outer side of a projection surface of the image pickup device and formed by unmounting surfaces on which a component is not mounted, the holding member holds the pair of image pickup apparatuses such that the surface sections projecting toward the outer side of the projection surface are opposed to one another on a parallax direction inner side, and the substrate is a laminated substrate in which a plurality of circuit boards are laminated in the parallax direction.

2. The stereo image pickup unit according to claim 1, wherein, in the substrate, ground wires are connected to the surface sections opposed to each other on the parallax direction inner side and other signal wires are connected to the surface sections other than the surface sections opposed to each other on the parallax direction inner side.

3. The stereo image pickup unit according to claim 1, wherein the image pickup device included in each of the pair of image pickup apparatuses includes a cover glass, the holding member includes a single centering glass to which the cover glass is bonded, and the pair of image pickup apparatuses is held on the holding member by bonding the image pickup device to the holding member via the cover glass.

4. The stereo image pickup unit according to claim 1, wherein the pair of image pickup apparatuses is formed in a same shape each other and is held by the holding member in a state in which one of the image pickup apparatuses is rotated 180 degrees around an optical axis with respect to another of the image pickup apparatuses.

* * * * *